(12) United States Patent
McDougall et al.

(10) Patent No.: US 7,792,573 B2
(45) Date of Patent: Sep. 7, 2010

(54) METHOD FOR COLLECTING AND ASSIGNING PATIENT DATA IN A CLINICAL TRIAL

(75) Inventors: Robert Gregory McDougall, Fox Point, WI (US); Mark Robert Kohls, New Berlin, WI (US); Edmund Greaves, Brown Deer, WI (US)

(73) Assignee: General Electric Company, Schenectady, NY (US)

( * ) Notice: Subject to any disclaimer, the term of this patent is extended or adjusted under 35 U.S.C. 154(b) by 159 days.

(21) Appl. No.: 12/035,619

(22) Filed: Feb. 22, 2008

(65) Prior Publication Data

US 2009/0216139 A1 Aug. 27, 2009

(51) Int. Cl.
*A61B 5/04* (2006.01)
(52) U.S. Cl. .................................................. 600/509
(58) Field of Classification Search ............... 600/509; 704/9, 51; 707/3, 102; 709/201
See application file for complete search history.

(56) References Cited

U.S. PATENT DOCUMENTS

2006/0217623 A1* 9/2006 Morganroth ................ 600/509

OTHER PUBLICATIONS

Guidance For Industry—The Clinical Evaluation of QT/QTc Interval Prolongation and Proarrhythmic Potential for Non-Antiarrhythmic Drugs: ICH Topic E14, published by the Minister of Health, Canada, dated Apr. 4, 2006, currently found at http://www.hc-sc.gc.ca/dhp-mps/prodpharma/applic-demande/guide-Id/ich/efficac/e14-eng.php.*
Guidance For Industry—The Clinical Evaluation of QT/QTc Interval Prolongation and Proarrhythmic Potential for Non-Antiarrhythmic Drugs: ICH Topic E14 Published by the Minister of Health, Canada, dated Apr. 5, 2006.*
Hongwei Cai, Jielai Xia, Dezhong Xu, Donghuai Gao and Yongping Yan, A generic minimization random allocation and blinding system on web, Journal of Biomedical Informatics, vol. 39, Issue 6, Dec. 2006, pp. 706-719.

* cited by examiner

*Primary Examiner*—George Manuel
*Assistant Examiner*—Robert N Wieland
(74) *Attorney, Agent, or Firm*—Andrus, Sceales, Starke & Sawall, LLP

(57) ABSTRACT

A method for assigning an ECG for purposes of conducting a clinical trial is disclosed herein. The method includes assigning an ECG to a primary reader, selectively reassigning the ECG to the primary reader, and selectively assigning the ECG to a secondary reader. The method also includes automating the assignment of the ECG to a primary reader, automating the selective reassignment of the ECG to the primary reader, and/or automating the selective assignment of the ECG to a secondary reader in order to minimize manual labor requirements.

17 Claims, 3 Drawing Sheets

METHOD FOR COLLECTING AND ASSIGNING PATIENT DATA IN A CLINICAL TRIAL

BACKGROUND OF THE INVENTION

The subject matter disclosed herein relates to a method for collecting and assigning patient data for evaluation in a clinical trial.

One method for assessing the safety of a new medication involves the performance of a clinical trial. Clinical trials generally comprise a variety of different guidelines or requirements adapted to evaluate the safety of the medication in a reliable and consistent manner. As an example, the International Conference on Harmonisation of Technical Requirements for Registration of Pharmaceuticals for Human Use (ICH) has developed a series of guidelines for certain categories of clinical trials.

ICH document E14 provides recommendations concerning the design, conduct, analysis, and interpretation of clinical studies to assess the potential of a drug to delay cardiac repolarization. The E 14 recommendations include a manner for assigning patient electrocardiogram (ECG) data to a group of readers such that the reliability and consistency of the reader's assessment is optimized. The ECG data, which may comprise tens of thousands of individual ECG recordings, is generally manually assigned to each reader. The problem is that the process of manually assigning the ECG data is time consuming and labor intensive.

BRIEF DESCRIPTION OF THE INVENTION

The above-mentioned shortcomings, disadvantages and problems are addressed herein which will be understood by reading and understanding the following specification.

In an embodiment, a method includes assigning an ECG to a primary reader, selectively reassigning the ECG to the primary reader, and selectively assigning the ECG to a secondary reader. The method also includes automating the assignment of the ECG to a primary reader, automating the selective reassignment of the ECG to the primary reader, and/or automating the selective assignment of the ECG to a secondary reader in order to minimize manual labor requirements associated with the performance of a clinical trial.

In another embodiment, a method includes acquiring an ECG from a patient, performing an initial analysis of the ECG, and assigning the ECG to a primary reader. The method also includes selectively reassigning the ECG to the primary reader based on a predetermined intra-read percentage, and selectively assigning the ECG to a secondary reader based on a predetermined inter-read percentage. The method also includes automating the assignment of the ECG to a primary reader, automating the selective reassignment of the ECG to the primary reader, and/or automating the selective assignment of the ECG to a secondary reader in order to minimize manual labor requirements associated with the performance of a clinical trial.

In another embodiment, a method adapted to facilitate the performance of a clinical trial in compliance with ICH document E14 includes providing a reader list, and acquiring an ECG from a patient. The method also includes assigning the ECG to a first reader from the reader list if the ECG is the first acquired from the patient during the course of the clinical trial. The method also includes assigning the ECG to a primary reader if the ECG is not the first acquired from the patient during the course of the clinical trial. The method also includes selectively reassigning the ECG to the first reader or the primary reader based on a predetermined intra-read percentage, and selectively assigning the ECG to a second reader from the reader list based on a predetermined inter-read percentage. The method also includes automating the assignment of the ECG to the first reader, automating the assignment of the ECG to the primary reader, automating the selective reassignment of the ECG, and/or automating the selective assignment of the ECG to the second reader in order to minimize manual labor requirements.

Various other features, objects, and advantages of the invention will be made apparent to those skilled in the art from the accompanying drawings and detailed description thereof.

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Figure 1:
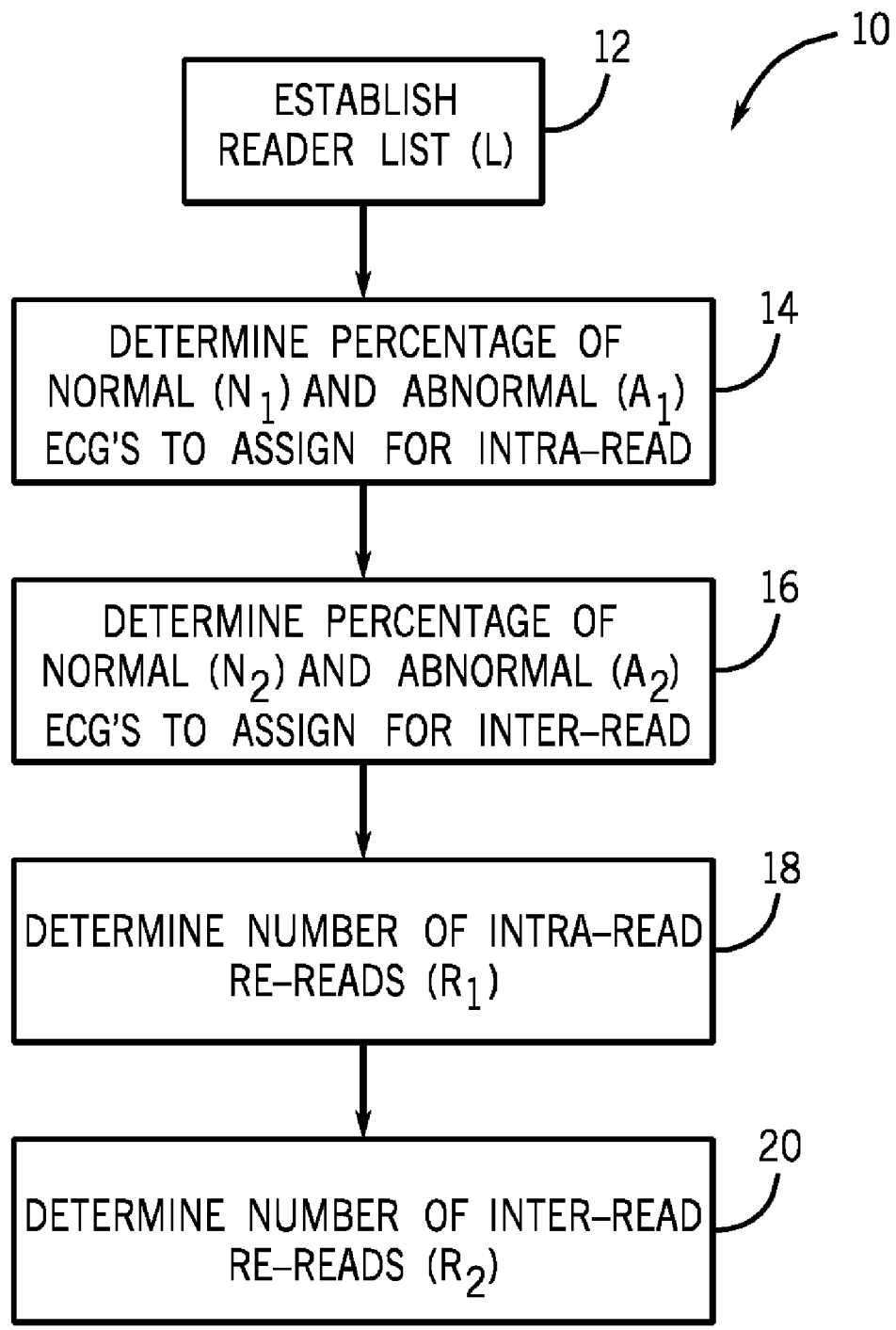
FIG. 1 is a flow chart illustrating a method for setting up a clinical trial in accordance with an embodiment.

Referring to FIG. 1, a flow chart illustrates a method 10 for setting up a clinical trial in compliance with document E14 from the International Conference on Harmonisation of Technical Requirements for Registration of Pharmaceuticals for Human Use (ICH). As is known to those skilled in the art, ICH document E14 pertains to the clinical evaluation of QT/QTc interval prolongation and proarrhythmic potential for non-antiarrhythmic drugs. The method 10 includes blocks 12-20 which represent steps that are generally manually performed. Steps 12-20 need not necessarily be performed in the order shown.

At step 12 of the method 10, a reader list L is established. The readers are generally physicians trained to evaluate an electrocardiogram (ECG). For purposes of this disclosure, an ECG is defined in a non-limiting manner to include one or more of the following: a recording of the electrical activity of the heart over time; patient demographic information (e.g. patient name or initials, patient identifier, age, gender, etc.); test demographic information (e.g. date and time of the recording, technician identification, etc.); interpretations; analysis; and measurements. In a non-limiting manner, the evaluation of the ECG data may comprise measuring the QT/QTc interval, and performing a morphological analysis.

At step 14, an "intra-read percentage" identifying the percentage of ECG's that should be intra-read is selected. Intra-read ECG's are those that are reassigned to the primary reader such that the same person evaluates the intra-read ECG's two or more times. Intra-reading may be implemented to evaluate the primary reader's consistency of analysis. For purposes of this disclosure, the "primary reader" is the reader selected from the reader list L that is initially assigned to read the first ECG obtained for a given patient during the course of the clinical trial. In other words, each patient will generally have multiple ECG's acquired during the course of the clinical trial, and the reader to whom the first ECG is initially assigned is deemed the primary reader.

The intra-read ECG's are generally blinded in order to minimize primary reader bias. For purposes of this disclosure, the term "blinding" refers to the process of hiding specific fields or types of data such as, for example, the patient's identity and any previously acquired medical analysis.

According to one embodiment, the intra-read percentage selected at step 14 comprises a normal intra-read percentage N1 and an abnormal intra-read percentage A1. The normal intra-read percentage N1 refers to the percentage of ECG's classified as being "normal" that should be reassigned to the primary reader. The abnormal intra-read percentage A1 refers to the percentage of ECG's classified as being "abnormal" that should be reassigned to the primary reader. The classification of an ECG as either normal or abnormal will be described in detail with respect to step 34 of the method 30 (shown in FIG. 2). Typical intra-read percentages range from 3-5%, however, it should be appreciated that other intra-read percentages may be selected to meet the needs of a particular clinical study.

At step 16, an "inter-read percentage" identifying the percentage of ECG's that should be inter-read is selected. Inter-read ECG's are those that are assigned to a secondary reader such that a different person evaluates the inter-read ECG's one or more times. Inter-reading may be implemented to provide a second opinion and thereby evaluate the primary reader's accuracy of analysis. For purposes of this disclosure, a "secondary reader" is a reader selected from the reader list L that is assigned to review an ECG that has previously been evaluated by the primary reader. The inter-read ECG's are generally blinded in order to minimize secondary reader bias.

According to one embodiment, the inter-read percentage selected at step 16 comprises a normal inter-read percentage N2 and an abnormal inter-read percentage A2. The normal inter-read percentage N2 refers to the percentage of ECG's classified as being "normal" that should be assigned to a secondary reader. The abnormal inter-read percentage A2 refers to the percentage of ECG's classified as being "abnormal" that should be assigned to a secondary reader. The classification of an ECG as either normal or abnormal will be described in detail with respect to step 34 of the method 30 (shown in FIG. 2). Typical inter-read percentages range from 3-5%, however, it should be appreciated that other inter-read percentages may be selected to meet the needs of a particular clinical study.

At step 18, the number of intra-read re-reads R1 is selected. The number of intra-read re-reads refers to the number of times an intra-read ECG should be reassigned to the primary reader. As an example, if the number of intra-read re-reads is three, the intra-read ECG will be reassigned to the primary reader three times. At step 20, the number of inter-read re-reads R2 is selected. The number of inter-read re-reads refers to the number of times an inter-read ECG should be assigned to a secondary reader. As the intra-read ECG's and the inter-read ECG's are generally blinded, the readers should be unaware that the same ECG is being reviewed multiple times.

Figure 2:
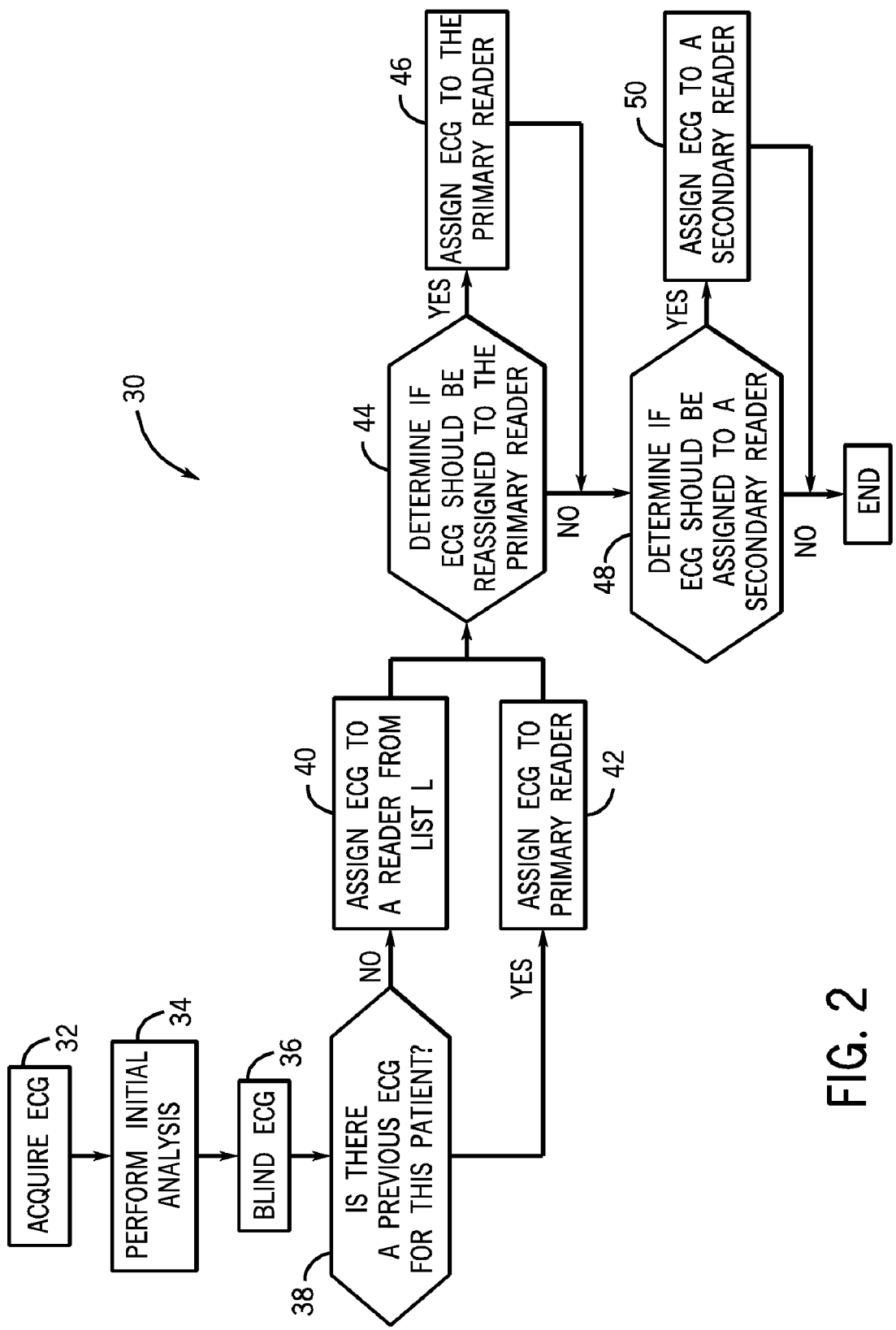
FIG. 2 is a flow chart illustrating a method for collecting and assigning patient ECG data in accordance with an embodiment.

Referring to FIG. 2, a flow chart illustrating a method 30 for collecting and assigning patient ECG data is shown in accordance with an embodiment. The method 30 is adapted to comply with the ICH document E14. The method 30 includes blocks 32-50 which represent steps that are generally automatically performed. Steps 32-50 need not necessarily be performed in the order shown, and some of the steps 32-50 may be optional. For purposes of this disclosure, the terms "automatic" and "automated" refer to steps or processes that are primarily performed by a device such as a computer, a controller, a processor, etc., and thereby require minimal manual intervention.

At step 32, an ECG is acquired from a patient P. In a non-limiting manner, the ECG may be acquired via a resting ECG recorder, a Holter recorder, or any other known ECG recording device.

At step 34, an initial analysis of the ECG acquired at step 32 is performed. The initial analysis of the ECG generally includes an automated measurement of the QT/QTc interval performed by a computer algorithm. The use of a computer algorithm to measure the QT/QTc interval or otherwise evaluate an ECG is known to those skilled in the art and therefore will not be described in detail. Alternatively, the analysis of the ECG at step 34 may be manually performed. The ECG analysis at step 34 typically classifies each ECG as being either "normal" or "abnormal".

At step 36, the ECG is blinded. As previously described, the term "blinding" refers to the process of hiding specific fields or types of data such as, for example, the patient's identity and any previously acquired medical analysis. It should be appreciated that this step is an optional step that may be implemented to minimize reader bias.

At step 38, the method 30 determines if a previous ECG has been acquired from the patient P during the course of the clinical trial. If a previous ECG has not been acquired from the patient P, the method 30 proceeds to step 40. If a previous ECG has been acquired from the patient P, the method 30 proceeds to step 42. At step 40, the ECG acquired at step 32 is assigned to a reader from the reader list L. The ECG assignment is generally random such that each reader on the reader list L has an equal chance of receiving the ECG. At step 42, the ECG acquired at step 32 is assigned to the primary reader for the patient P. Step 42 complies with the ICH document E14 guideline providing that a single reader should evaluate every ECG from a given patient.

At step 44, the method 30 determines if the ECG acquired at step 32 should be reassigned to the primary reader. This determination may be predicated on the intra-read percentages N1 and A1. More precisely, if the initial analysis performed at step 34 classifies the ECG as "normal", the intra-read percentage N1 may be implemented to determine if the ECG should be reassigned to the primary reader. Similarly, if the initial analysis performed at step 34 classifies the ECG as "abnormal", the intra-read percentage A1 may be implemented to determine if the ECG should be reassigned to the primary reader. According to one embodiment, the method 30 may generate a random number within the range of 1 to 100 and compare the randomly generated number with the appropriate intra-read percentage (i.e., either N1 or A1) in order to determine if the ECG acquired at step 32 should be reassigned to the primary reader. If it is determined at step 44 that a given ECG should be reassigned to the primary reader, the method 30 proceeds to step 46. If it is determined at step 44 that a given ECG should not be reassigned to the primary reader, the method 30 proceeds to step 48.

At step 46, the ECG acquired at step 32 is reassigned to the primary reader. The ECG can be reassigned to the primary reader R1 times in order to comply with the number of intra-read re-reads selected at step 18 of the method 10 (shown in FIG. 1). Multiple assignments can be spaced out over a period of time and/or included blinded ECG's such that the primary reader is unaware that the same ECG is being reviewed.

At step 48, the method 30 determines if the ECG acquired at step 32 should be assigned to a secondary reader. This determination may be predicated on the inter-read percentages N2 and A2. More precisely, if the initial analysis performed at step 34 classifies the ECG as "normal", the inter-read percentage N2 may be implemented to determine if the ECG should be assigned to a secondary reader. Similarly, if the initial analysis performed at step 34 classifies the ECG as "abnormal", the inter-read percentage A2 may be implemented to determine if the ECG should be assigned to a secondary reader. According to one embodiment, the method 30 may generate a random number within the range of 1 to 100 and compare the randomly generated number with the appropriate inter-read percentage (i.e., either N2 or A2) in order to determine if the ECG acquired at step 32 should be assigned to a secondary reader. If it is determined at step 48 that a given ECG should be assigned to a secondary reader, the method 30 proceeds to step 50. If it is determined at step 48 that a given ECG should not be assigned to a secondary reader, the method 30 terminates with respect to this particular ECG.

At step 50, the ECG acquired at step 32 is assigned to a secondary reader. According to one embodiment, the ECG can be assigned one time each to R2 different secondary readers. According to another embodiment, the ECG can be assigned to a single secondary reader R2 times. Multiple assignments can be spaced out over a period of time and/or included blinded ECG's such that the secondary reader is unaware that the same ECG is being reviewed.

Figure 3:
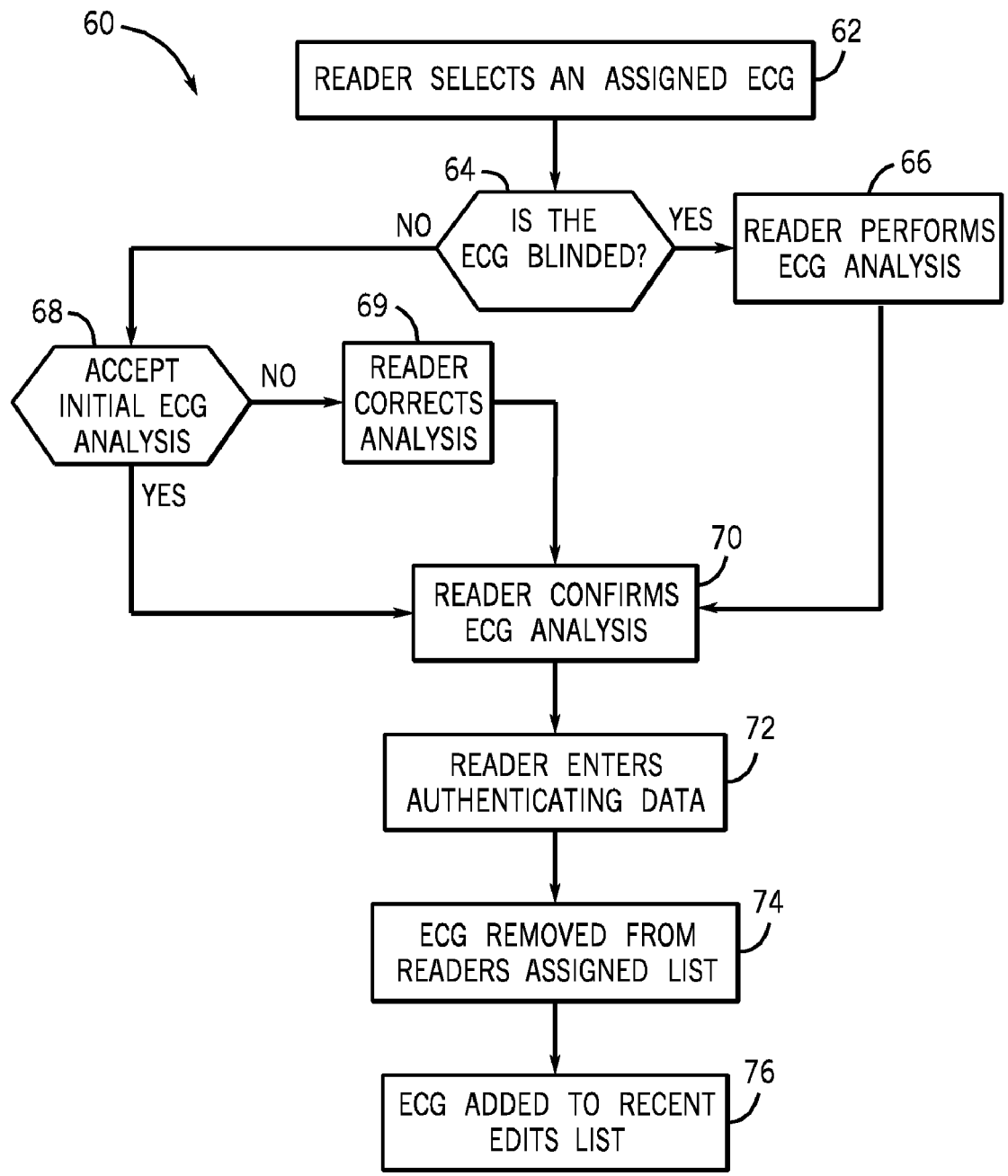
FIG. 3 is a flow chart illustrating a method for reading and evaluating a plurality of assigned ECG's in accordance with an embodiment.

Referring to FIG. 3, a flow chart illustrates a method 60 for reading and evaluating a plurality of assigned ECG's. The method 60 is particularly well suited for systematically reading ECG's assigned in accordance with the method 30 (shown in FIG. 2). The method 60 includes blocks 62-76 which represent a series of steps. Steps 62-76 need not necessarily be performed in the order shown.

At step 62, a reader selects an assigned ECG. It should be appreciated that the assigned ECG's are generally stored in the form of an assignment list that is disposed on a database and made available exclusively to the appropriate reader. Accordingly, the process of selecting an assigned ECG at step 62 typically requires a reader to log into the database and select one of the assigned ECG's from their assignment list.

At step 64, the method 60 determines whether the ECG has been blinded. If the ECG is blinded, the method 60 proceeds to step 66. If the ECG is not blinded, the method 60 proceeds to step 68. At step 66, the reader analyzes the selected ECG. In a non-limiting manner, the reader's analysis may include a QT/QTc interval measurement and a morphological analysis.

At step 68, the reader decides whether or not to accept any initial ECG analysis such as that performed during step 34 of the method 30 (shown in FIG. 2). The initial ECG analysis is generally accepted if it is consistent with the reader's analysis, and is rejected if it is inconsistent with the reader's analysis. If the reader does not accept the initial ECG analysis, the method 60 proceeds to step 69. If the reader does accept the initial ECG analysis, the method 60 proceeds to step 70.

At step 69, the initial ECG analysis is corrected or revised so that it complies with the reader's analysis. At step 70, the reader confirms final ECG analysis. Step 70 is an optional step that may be implemented to verify the reader's intent to submit and thereby reduce the likelihood that an incomplete ECG analysis is unintentionally submitted. At step 72, the reader enters authenticating data such as, for example, the reader's identity and a password. Step 72 is also an optional step that may be implemented to verify the identity of a particular reader. Step 72 may also be implemented to comply with Code of Federal Regulations (CFR) title 21 part 11 Electronic Records and Signatures requirements.

At step 74, the analyzed ECG is removed from the reader's assignment list. At step 76, the analyzed ECG is added to a recent edits list. Step 76 is optional and may be implemented to allow a reader to review or revisit a recently submitted ECG. Step 76 is particularly useful for use with blinded ECG's as it would otherwise be difficult identify a recently submitted ECG to be reviewed.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

We claim:

1. A method comprising:
   receiving an intra-read percentage;
   receiving an inter-read percentage;
   assigning an electrocardiogram (ECG) to a primary reader;
   receiving a first evaluation of the ECG from the primary reader;
   selectively reassigning the ECG to the primary reader based upon the received intra-read percentage;
   receiving a second evaluation of the ECG from the primary reader;
   selectively assigning the ECG to a secondary reader based upon the received inter-read percentage; and
   receiving a third evaluation of the ECG from the secondary reader;
   wherein one or more of said assigning the ECG to a primary reader, selectively reassigning the ECG to the primary reader, and selectively assigning the ECG to a secondary reader is automated in order to minimize manual labor requirements associated with the performance of a clinical trial.

2. The method of claim 1, further comprising blinding the ECG before said assigning the ECG to the primary reader.

3. The method of claim 1, further comprising:
   performing an automated measurement of an interval of the ECG; and
   classifying the ECG based upon the automated measurement.

4. The method of claim 3, wherein the received intra-read percentage includes a normal ECG intra-read percentage and an abnormal ECG intra-read percentage and said selectively reassigning the ECG to the primary reader based on the received intra-read percentage comprises selectively reassigning the ECG to the primary reader based on the normal ECG intra-read percentage, abnormal ECG intra-read percentage and the ECG classification based upon the automated measurement.

5. The method of claim 3, wherein the received inter-read percentage includes a normal ECG inter-read percentage and an abnormal ECG inter-read percentage and said selectively assigning the ECG to the secondary reader based on the received inter-read percentage comprises selectively assigning the ECG to the secondary reader based on the normal ECG inter-read percentage, abnormal ECG inter-read percentage, and the ECG classification based upon the automated measurement.

6. The method of claim 1, further comprising:
receiving a selection of an intra-read number; and
repeating the selective reassignment of the ECG the intra-read number of times.

7. The method of claim 1, further comprising:
receiving a selection of an inter-read number; and
selectively assigning the ECG the inter-read number of times.

8. A method comprising:
acquiring an ECG from a patient;
automatedly performing an initial analysis of the ECG including a measurement of an interval of the ECG;
assigning the ECG to a primary reader;
presenting the ECG to the primary reader;
receiving a first evaluation of the ECG from the primary reader;
receiving an intra-read percentage;
selectively reassigning the ECG to the primary reader based on a the intra-read percentage; presenting the ECG to the primary reader;
receiving a second evaluation of the ECG from the primary reader;
receiving an inter-read percentage;
selectively assigning the ECG to a secondary reader based on the inter-read percentage;
presenting the ECG to the secondary reader; and
receiving a third evaluation of the ECG from the secondary reader;
wherein said selectively reassigning the ECG to the primary reader; and said selectively assigning the ECG to the secondary reader are automated in order to minimize manual labor requirements associated with the performance of a clinical trial.

9. The method of claim 8, further comprising blinding the ECG before said assigning the ECG to the primary reader.

10. The method of claim 8, wherein the received intra-read percentage comprises a normal intra-read percentage and an abnormal intra-read percentage, and said selectively reassigning the ECG to the primary reader based on a predetermined intra-read percentage comprises selectively reassigning the ECG to the primary reader based on the initial analysis of the ECG, the normal intra-read percentage, and abnormal intra-read percentage.

11. The method of claim 8, wherein the received inter-read percentage comprises a normal inter-read percentage and an abnormal inter-read percentage, and said selectively assigning the ECG to the secondary reader based on a predetermined inter-read percentage comprises selectively assigning the ECG to the secondary reader based on the initial analysis of the ECG, the normal inter-read percentage, and a the abnormal inter-read percentage.

12. The method of claim 10, wherein said selectively reassigning the ECG is further based upon the received first evaluation of the ECG from the primary reader.

13. The method of claim 11, wherein said selectively assigning the ECG is further based upon the received first and second evaluations of the ECG from the primary reader.

14. A method adapted to facilitate the performance of a clinical trial in compliance with ICH document E14, said method comprising:
providing a reader list;
acquiring an ECG from a patient;
automatically blinding the ECG;
assigning the ECG to a first reader from the reader list if the ECG is the first acquired from the patient during the course of the clinical trial;
assigning the ECG to a primary reader if the ECG is not the first acquired from the patient during the course of the clinical trial;
selectively reassigning the ECG to the first reader or the primary reader based on a predetermined intra-read percentage; and
selectively assigning the ECG to a second reader from the reader list based on a predetermined inter-read percentage;
wherein one or more of said assigning the ECG to a first reader; assigning the ECG to a primary reader; selectively reassigning the ECG; and selectively assigning the ECG to a second reader is automated in order to minimize manual labor requirements.

15. The method of claim 14, further comprising performing an initial analysis of the ECG.

16. The method of claim 14, wherein said selectively reassigning the ECG comprises selectively reassigning the ECG a selectable number of times based on a predetermined number of intra-read re-reads.

17. The method of claim 14, wherein said selectively assigning the ECG comprises selectively assigning the ECG a selectable number of times based on a predetermined number of inter-read re-reads.

* * * * *